(12) United States Patent
Zuest et al.

(10) Patent No.: US 9,329,375 B2
(45) Date of Patent: May 3, 2016

(54) MICROSCOPE HAVING A TOUCH SCREEN

(75) Inventors: Reto Zuest, Widnau (CH); Ruedi Rottermann, Berneck (CH); Harald Schnitzler, Luechingen (CH); Robert Lettow, Winterthur (CH)

(73) Assignee: LEICA MICROSYSTEMS (SCHWEIZ) AG, Heerbrugg (CH)

(*) Notice: Subject to any disclaimer, the term of this patent is extended or adjusted under 35 U.S.C. 154(b) by 1114 days.

(21) Appl. No.: 13/294,390

(22) Filed: Nov. 11, 2011

(65) Prior Publication Data
US 2012/0120224 A1 May 17, 2012

(30) Foreign Application Priority Data

Nov. 15, 2010 (DE) .......................... 10 2010 043 942
Dec. 17, 2010 (DE) .......................... 10 2010 063 392

(51) Int. Cl.
*H04N 7/18* (2006.01)
*G02B 21/24* (2006.01)
*G02B 21/00* (2006.01)
*G02B 21/36* (2006.01)
*G06F 19/00* (2011.01)

(52) U.S. Cl.
CPC ............ *G02B 21/24* (2013.01); *G02B 21/0016* (2013.01); *G02B 21/368* (2013.01); *G06F 19/3406* (2013.01)

(58) Field of Classification Search
CPC .. G02B 21/00; G02B 21/365; G02B 21/0016; G02B 21/24; G02B 21/368; G06F 19/3406
USPC .......................... 348/79, 77, E7.085; 359/368
See application file for complete search history.

(56) References Cited

U.S. PATENT DOCUMENTS

| | | | |
|---|---|---|---|
| 8,466,958 B2* | 6/2013 | Shirota et al. .................... | 348/77 |
| 2002/0015224 A1 | 2/2002 | Ganser | |
| 2005/0111087 A1 | 5/2005 | Knoblich et al. | |
| 2007/0226646 A1* | 9/2007 | Nagiyama et al. ............. | 715/784 |
| 2010/0194874 A1* | 8/2010 | Bierhoff et al. .................. | 348/80 |
| 2011/0113329 A1* | 5/2011 | Pusateri ........................ | 715/702 |
| 2011/0141262 A1 | 6/2011 | Ernsperger et al. | |
| 2015/0199053 A1 | 7/2015 | Hotelling et al. | |

FOREIGN PATENT DOCUMENTS

| | | |
|---|---|---|
| CN | 1942853 A | 4/2007 |
| DE | 200 13 359 U1 | 11/2000 |
| DE | 102008028482 A1 | 12/2009 |
| EP | 1 533 643 A1 | 5/2005 |
| JP | 07181393 A | 7/1995 |
| JP | 7244243 A | 9/1995 |
| JP | 08146302 A | 6/1996 |
| JP | 08223563 A | 8/1996 |

(Continued)

*Primary Examiner* — William C Vaughn, Jr.
*Assistant Examiner* — Naod Belai
(74) *Attorney, Agent, or Firm* — Leydig, Voit & Mayer, Ltd.

(57) ABSTRACT

A microscope includes an image acquisition system, microscope components and a touch screen. The image acquisition system is configured to optically and digitally image an object so as to produce an object image The microscope components are at least one of motorized and electrically controllable. The touch screen is configured to display the object image in a display area thereof and to sense inputs in the display area within the displayed object image so as to change settings of the microscope components.

27 Claims, 6 Drawing Sheets

(56) References Cited

FOREIGN PATENT DOCUMENTS

| JP | 09197287 A | 7/1997 |
| JP | 2000163031 A | 6/2000 |
| JP | 2002281365 A | 9/2002 |
| JP | 2009239424 A | 10/2009 |
| JP | 2010258878 A | 11/2010 |
| WO | WO 96/18924 A1 | 6/1996 |

* cited by examiner

MICROSCOPE HAVING A TOUCH SCREEN

CROSS REFERENCE TO RELATED APPLICATIONS

This application claims priority to German Patent Application No. 10 2010 043 942.8, filed on Nov. 15, 2010, and German Patent Application No. 10 2010 063 392.5, filed on Dec. 17, 2010, both of which are hereby incorporated by reference herein in their entirety.

DESCRIPTION

The present invention relates to a microscope having a touch screen, and to an associated control device and a corresponding operating method.

BACKGROUND

In microscopy, the objects observed, for example during examination of samples for purposes of manufacturing quality control or medical analysis, are typically of a size exceeding that of the field of view of the microscope objective used. It is therefore common practice in microscopy to first find the sample region to be examined ("region of interest") at low magnification and position it in the center of the field of view. Then, the magnification is increased in order for details in the respective region to be examined, measured, documented or, in particular, subjected to image processing for feature extraction. In order to find further such sample regions, it is necessary to reduce the magnification again.

For the purposes mentioned, conventional microscopes are provided with, for example, manual cross-stages and/or rotary stages and/or devices for magnification adjustment, such as objective turrets or zoom systems, or other motorized devices of this kind.

The aforementioned steps turn out to be complex and not very intuitive, especially when it comes to routine examination, because the adjustment processes mentioned do not directly correspond to the natural viewing of objects.

For routine microscopy, automated microscope systems, such as described, for example, in DE 200 13 359 U1, are provided with control and power supply means in an external unit.

External units for entering operating and control commands for observation devices are also described, for example, in EP 1 533 643 A1. Such units may, for example, be in the form of a screen, such as a touch screen, as a means for displaying setting values and/or an object being viewed or a process sequence.

Moreover, documents WO 96/18924 A1 and JP 07244243 A, inter alia, describe touch screens for controlling microscopes. In an approach such as the one proposed in the JP 07244243 A the image display area is reduced because of the size of the control elements provided, which are always visible on the touch screen.

However, the control units for microscopes and the associated methods known from the prior art are suitable only to a very limited extent for the aforementioned tasks and do not allow samples to be examined in an efficient, intuitive and cost-effective manner.

Therefore, there continues to be a need for methods for controlling the operation of microscopes that overcome the disadvantages of the prior art.

SUMMARY

In an embodiment, the present invention provides a microscope including an image acquisition system, microscope components and a touch screen. The image acquisition system is configured to optically and digitally image an object so as to produce an object image The microscope components are at least one of motorized and electrically controllable. The touch screen is configured to display the object image in a display area thereof and to sense inputs in the display area within the displayed object image so as to change settings of the microscope components.

BRIEF DESCRIPTION OF THE DRAWINGS

Exemplary embodiments of the present invention will be described in more detail below with reference to the drawings, in which.

DETAILED DESCRIPTION

Although the present invention is described in this application with particular reference to video microscopy, it will be understood that the features of the present invention may also be used in other imaging systems for examining objects. When the term "microscope" is used in this application, it is intended to include, in particular, so-called macroscopes, stereomicroscopes, stereo magnifiers, and the like.

Further advantages and embodiments of the present invention will become apparent from the description and the accompanying drawings.

It will be understood that the aforementioned features and those described below, especially in connection with the exemplary embodiments, can be used not only in the specified combinations, but also in other combinations or alone without departing from the scope of the present invention.

In an embodiment, the present invention provides a microscope and an associated control device as well as a corresponding operating method.

In an embodiment present invention is directed to a microscope including an image acquisition system adapted for optically and digitally imaging an object to produce an object image. The image acquisition system is typically composed of optical and digital components and has means for optically and/or digitally magnifying or reducing the object image produced (which is known as optical and digital zoom, respectively). Moreover, there are advantageously provided means for digitally processing the captured image, for example, to improve contrast. In a practical example, the image acquisition system of the prior art microscope includes well-known optical components, such as objective, zoom system and/or magnification changer, tube, focus drive, microscope stage (cross stage or rotary stage), illumination devices, and, possibly, one or two eyepieces. The image acquisition system further includes digital components, such as a camera, and, possibly, an image processing system. The camera has a light-sensitive electronic device in the form of a sensor matrix. A typical embodiment of such a device is a CCD or CMOS chip. Often, the image acquisition system has an integrated digital image processing system. While the optical components of the image acquisition system produce an object image of selectable magnification, the digital components are used for processing the image data to subsequently display them in the form of an object image on a screen.

In the case of what is called a "live image", any change to the microscope components, in particular to the aforementioned components of the image acquisition system, results in a change in the displayed object image. In contrast, in the case of a "still image", changes in the displayed object image are made by manipulating the stored image.

In accordance with an embodiment of the present invention, a microscope of the type under discussion has a touch screen adapted to display the object image in a display area and to sense user inputs in the display area, the microscope being adapted to allow settings of motorized and/or electrically controllable microscope components to be changed on the microscope based on the inputs sensed in the display area of the touch screen; i.e., within the displayed object image. The term "object image", as used above and hereinafter, is understood to mean, in the first place, a live image or, in the second place, a still image.

An ergonomically particularly beneficial, and therefore preferred, embodiment is obtained in the live image function of the microscope: inputs made within the displayed object image; i.e., manipulations of this object image, can be directly converted into corresponding changes of the settings of microscope components, so that the new live image corresponds to the desired image result. The microscope components adjusted as a result of the aforementioned inputs include, in particular, the digital components of the image acquisition system, such as camera, sensor and an image processing system, as well as the optical components of the image acquisition system, such as objective, zoom system and/or magnification changer, focus drive, tube, illumination devices, microscope stage (cross stage or rotary stage), and, possibly, eyepieces. Thus, in this preferred embodiment of the present invention, an input in the live image leads to a new image result, which is produced by adjustment of the microscope components mentioned. Thus, the new image result is not obtained by manipulating the stored image, for example, by means of digital image shift, image rotation or digital zoom, but by operating the optical and/or digital microscope components, including the microscope stage.

Several examples are given to illustrate this preferred embodiment of the present invention. In the described intuitive and ergonomically particularly convenient method of controlling the microscope, movement of the contact point in the object image displayed on the touch screen causes the motorized stage to be translated in such a way that the new live image corresponds to the desired image result of a shifted object image. Rotation of a detail in the object image in the simplest case causes the stage to be rotated in such a way that the new live image corresponds to the desired image result of a rotated object image. Additionally or alternatively, the rotation of a live image may be performed by the image processing system by means of instant coordinate transformation, especially if no rotary stage is available. A change of the distance between two contact points in the object image may cause the zoom system and/or magnification changer to zoom in such a way that the new live image corresponds to the desired image result of an object image that is displayed at a changed magnification. Continuous contact of the selected input means with the object image without moving the selected input means causes, for example, an adjustment of the (auto-) focus, while shorter contact results in storage of a live image (as a still image). Further embodiments of such intuitive control options are illustrated in the following description and examples. In some cases of application, such as, for example, the above-described rotation of the object image, it may be necessary and/or advantageous to use the above-mentioned digital components of the image acquisition system in addition to and in conjunction with the above-mentioned optical microscope components, including the microscope stage, in order to optimally readjust all microscope components in such a way that the image result corresponds to the desired live image.

Thus, unlike the prior art, which at most allows device parameters, such as zoom and focus settings, to be selected and adjusted via suitable touch screen fields that are located outside the displayed object image, embodiments of the present invention allow for inputs sensed by the touch screen to be implemented directly within the displayed object image. For this purpose, the object image, which is captured by an image acquisition system, first in analog and then in digital form, and advantageously already suitably processed, is displayed in a display area on the touch screen. In accordance with an embodiment of the present invention, a user can then make entries directly on the displayed object image using suitable input means. In the simplest case, and provided that the touch screen is suitably designed, the user can do this using his or her fingers, but alternatively also with the aid of input pens, infrared pointers, and the like. Given a suitable instrument configuration, these inputs, such as, for example, touches of short or longer duration, gestures, linear and/or rotational motions, can be converted into settings for microscope components.

Such direct conversion of inputs into, for example, a movement of an object, image or image region in a microscope has not been described heretofore.

Further, heretofore, the prior art has only described separate control units which have to be provided as separate components and, therefore, add to the manufacturing cost of a microscope. Moreover, such separate units require a more complex system setup and increase the space requirements for such an approach. Therefore, it is advantageous for the image acquisition system and the touch screen to be designed as an integral unit.

In contrast to an approach with a reduced image display area caused by the size of control elements that are always visible on the touch screen, in an approach of the present invention, the entire image display area is available as an input unit. Of course, the present invention does not preclude the use of additional operator control units, such as joysticks, input buttons, cursor keys, keypads, rotary controls, foot switches, and the like.

A touch screen of the type under discussion is advantageously adapted, at least in the display area, to sense a position, a motion, and/or an acceleration of at least one input means on or near its surface. This makes it possible to detect contact of a finger or other input means with the surface during a short or longer period of time, or to detect motion of the input means while in contact with the surface (which is referred to as a "touch-and-move" operation).

In this connection, it is convenient that control signals capable of controlling the functions of the motorized and/or electrically controllable microscope components be derived from the sensed position, motion and/or acceleration of the at least one input means.

The aforesaid motorized and/or electrically controllable microscope components include: the above-mentioned image acquisition system, in particular the imaging sensor or a digital camera, an image processing system, which can be a separate unit or integrated with the aforementioned sensor or the digital camera, control and/or processing means, an objective turret having at least one objective, a motorized zoom adjustment, a focus drive movable in the z-direction to adjust the focus of the microscope, an x-y adjustable microscope stage, in particular a cross-stage, and/or a microscope stage designed as a rotary stage. In particular, the motorized and/or electrically controllable microscope components can correspond to the digital and optical components of the image acquisition system which were mentioned earlier herein. The components mentioned have already been described in the introductory part of the description and their design and operation are generally known to those skilled in the art of microscopy.

It is also advantageous for a touch screen of the type under discussion to be provided, at least in the display area, with means for sensing a relative position, a relative motion and/or a relative acceleration of several input means with respect to one another on or near its surface. This makes it possible to detect, for example, contact of several input means with the screen, on the basis of which a zoom command and/or a rotation command, for example, can be recognized, as will be described in more detail further below.

It is considered advantageous to provide the microscope with a fully functional multi-touch screen, so that all possible input modes that can be implemented by such screens can be made use of.

A touch screen of the type under discussion is provided, at least in the display area, with acoustic pulse and/or surface-wave sensors (especially for multi-touch operation), capacitive sensors (e.g., surface-capacitive sensors or projected capacitive sensors, in particular single layer ones), bending wave sensors, resistive sensors (e.g., 5-wire and/or 4-wire resistive sensors), optical sensors (e.g., shadow sensors) and/or infrared sensors for sensing the inputs. Such sensors, and touch screens provided with such sensors, are produced in high quantities, and therefore, are available at low cost.

A microscope in which the present invention is implemented can advantageously include at least an object-moving device and/or an optical unit and/or a digital image processing system. A change to the above-mentioned settings on the microscope affects the object-moving device, the optical unit and/or the digital image processing system. By using the proposed features, the effectiveness of a microscopic method which requires inspection of a plurality of image regions ("regions of interest") is improved, making the method particularly intuitive for the user.

Again, embodiments of the invention are not directed to only manipulating an object image by changing the settings of the stored image. However, such manipulation of the stored image may be advantageous in certain embodiments and may be used as an additional measure.

A basic function of the microscope may be one which displays a full live image of the observed object in the display area of the touch screen. In a basic input mode, lateral motions of one or more input means along the surface of the touch screen result in translational motion of the object image obtained.

In the process, either an image portion displayed by the image acquisition system may be shifted, or an object-moving device may be moved. In the latter case, a touch-and-move operation causes the object-moving device (e.g., a motorized cross-stage) to be moved to the desired position. The speed of movement of the object-moving device is directly correlated to the given movement of the input means. The respective directions of motion are opposed, as will be described in more detail further below. Similarly, rotation or zoom operations, for example, may also be implemented, as will also be further described hereinbelow.

A control device associated with such a microscope, can have an input for receiving inputs sensed by the touch screen at least in its display area, and at least one output for changing the settings on the microscope. As for the respective features, reference is made to the above explanations.

An operating method according to an embodiment of the present invention includes: sensing inputs in the display area of the touch screen and changing settings on the microscope based on the inputs sensed in the display area of the touch screen; i.e. inputs made directly on the displayed object image.

In such a method, the sensing of inputs advantageously includes recognizing translation commands, rotation commands, zoom commands, center commands, focus commands, selection commands, measurement commands, processing commands, integration commands and/or function change commands in the display area of the touch screen, so that all of these commands can be directly converted into corresponding settings.

It is advantageous to define different functions for the operation of the microscope. A convenient basic function of the microscope is a mode of operation in which a live image of the examined object is displayed. Another basic function is one which displays a still image. Yet another function may be used to perform autofocusing. Finally, it is possible to define more complex functions, such as measurement of an imaged object, image processing of the object image or portions thereof or, finally, providing the object image with annotations. It is useful that each an input mode be defined for and assigned to each selected function. An input mode is characterized in that the (relative) position, (relative) motion and/or (relative) acceleration of one or more input means are interpreted in a specific way to recognize a command therefrom.

In the case of the live image function, the commands entered via the touch screen are converted into control signals for controlling, for example, the image acquisition system, an imaging sensor or a digital camera, an image processing system, control and/or processing means, a motorized objective turret having at least one objective, a motorized zoom adjustment, a focus drive movable in the z-direction, a motorized, x-y adjustable microscope stage, in particular a cross-stage, and/or a motorized rotary stage.

In the case of the still image function, the commands entered via the touch screen are converted into control signals which control, for example, the image processing system and/or the control and/or processing means.

Furthermore, both in the live image mode and the still image mode, it may be possible to enter commands via the touch screen in order to switch from the live image function to the still function and/or vice versa, the switching between modes being accomplished by the control and/or processing means using the generated control signals.

Prior to discussing this in more detail, a simple example is given for illustration: It is convenient for the "live image" and "still image" basic functions to use the same input mode, in which, for example, a contact of the touch screen with the input means followed by dragging of the input means along a path ("touch and move") is recognized as a translation command (see further below for the conversion of the translation command). In contrast, the more complex measurement function uses a different input mode and, therefore, the same input is interpreted in a different way, for example, as a measurement command to measure the length of the path traveled by the input means in the object space.

In the basic function of the operation of the microscope, a translation command is advantageously recognized when at least one input means is positioned in contact with, or near, the surface of the display area of the touch screen and moved from there relative to the surface. Such a motion process corresponds to the natural motion sequence for moving a real object, which allows a very intuitive and easy control of a microscope.

In a similarly intuitive and, therefore, particularly advantageous manner, it may be provided for a rotation command to be recognized when a plurality of input means are positioned in contact with, or near, the surface of the display area of the touch screen and jointly rotated from there relative to the surface, for example, about a common center of rotation.

A zoom command is advantageously recognized when a plurality of input means are positioned in contact with, or near, the surface of the display area of the touch screen and the relative distance between the input means is changed. Conversion into microscope settings may, for example, consist in a change in the zoom factor of a zoomable optical unit or a captured digital image (optical or digital zoom). This motion of the input means, which corresponds to a "pulling apart motion" in reality, is also intuitive and immediately comprehensible to the user.

Especially the three commands mentioned (translation, rotation and zoom commands) enable highly effective and intuitive examination of samples on the basis of the live image, during which the region of interest is first searched for on the sample at low magnification in a complete view of the live image and, when found, is moved to the center of the field of view. These operations can be easily and intuitively performed using translation commands and, if necessary, rotation commands. Then, the magnification of the live image is increased to allow details of the region of interest to be examined in depth. This is done using the zoom command described above. After the examination, the magnification is reduced to switch to complete view. This is also done using the zoom command described above. The method returns to searching for another region of interest of the live image. During examination of the region of interest at high magnification, it is possible to select the above-mentioned more complex functions, such as, for example, the measurement function or the image processing function.

Generally speaking, any particular command, such as a translation command, zoom command, center command, focus command, measurement command, processing command, integration command and/or a function change command can, at any one time, be recognized when a defined number of input means are brought into contact with, or near, the surface of the display area, and/or maintained in contact with, or near, said surface, for a defined period of time, a defined number of times and/or at a defined number of positions. Inputs recognized in this manner include, for example, single, double and multiple touches (similar, for example, to single, double or multiple clicks of a computer mouse), touches of longer or shorter duration, faster or slower motions, or corresponding simple or more complex input sequences (long-short, short-long, etc.). All of these inputs can be converted into corresponding settings on the microscope, even in a user-definable manner. For example, a short touch (without motion) may trigger a still image ("snapshot"). On the other hand, a longer touch may trigger an autofocus operation.

In the method of an embodiment of the present invention, conversion into the corresponding instrument settings advantageously occurs in such a way that an object image produced by the optical components of the image acquisition system and/or an object imaged by digital components of the image acquisition system is/are translated, rotated, centered and/or focused when a translation command, a rotation command, a zoom command, a center command and/or a focus command is/are recognized in the display area of the touch screen.

Furthermore, in particular, gestures; i.e., motion patterns performed by input means on the surface of the image acquisition system in the display area, can be assigned to specific additional functions. For example, gestures may be used to display or hide control elements for more complex functions, such as measurement, image processing, annotation, and the like. Such a gesture may also be used, for example, to make a function change to a different mode of operation of the microscope; i.e., for example, to directly select one of the more complex functions mentioned. On the other hand, it is also possible to select such functions conventionally, using input elements specifically provided for this purpose.

As described earlier herein, the selection of such a more complex function can change the input mode of the touch screen. For example, the selection of a measurement function can change the input mode in such a way that a first touch by an input means defines a reference point (as the starting point of a measurement) and another reference point, which is also defined by an input means, indicates the endpoint of a scale defined between the two contact points. In other words, two contact points may be used to define a line for a distance measurement to be made using the microscope, each contact point constituting an endpoint of a measuring path. Similarly, three contact points, for example, may be used to define a measuring line for the measurement of an angle. Analogously, four contact points can define a circle within which to perform, for example, an area measurement, with each contact point being used for circle approximation. It is also possible to define a different geometry in place of a circle. In the measurement function, the above-described "touch and move" input operation can be used to define the contact points on the measuring line. These input modes have been mentioned merely by way of example and can be redefined without departing from the scope of the present invention.

On the other hand, if the image processing function is selected, a contact point may define a particular image processing mode. For example, a region defined by a contact point located therein may be selected or defined for an image processing operation. Then, it is possible to perform, for example, binarization (black-and-white representation) or generate a false color representation within this region.

When an annotation function is selected, the annotation can be defined or changed using the above-described "touch and move" input operation. Such an input operation changes, for example, the position, size and orientation of the annotation. If a text annotation is desired, a keyboard may be displayed in the display area, for example, by a specific touch in a text region.

In a method of the type under discussion, it is also advantageous if a region of an object image produced by the image acquisition system is selected, measured, processed and/or integrated when a selection command, a measurement command, a processing command and/or an integration command is recognized in the display area of the touch screen. It is useful to offer the above-mentioned commands to the user while the object is examined at high magnification. The selection command, for example, may be recognized when a specific object region within the region of interest is encircled. The selection command may, for example, cause the selected object region to be bordered and/or highlighted in color. Various measurement and processing commands have already been described above in connection with the corresponding measurement and image processing functions. An integration command may be defined to be recognized, for example, when a single tap or a multiple tap is performed on the selected region within a specific time window after a selection command. The integration command results in surface integration being performed on the area of the selected region in the object space; i.e., in the determination of the area of the selected continuous object region by means of image processing using thresholding or edge detection techniques. In the thresholding method, each pixel exceeding a certain brightness value (threshold) is considered to be part of the area and is considered in the integration. In edge detection, the boundary line for the integration is determined by defining, in each direction, an imaginary ray which originates at the contact point. The brightness profile of the pixels is plotted along this ray. The boundary line for the integration is then formed by a set of points consisting of one point from each brightness profile along the respective rays. On each ray, this point may be defined, for example, as the inflection point of the brightness profile.

As explained, it is also within the scope of this method to switch between functions and change the input mode accordingly (e.g., to switch from a measurement function to an image processing function) when a function change command is recognized, for example, from a gesture in the display area of the touch screen.

Similarly, the functions may be exited by a further function change command; i.e., by another input gesture, so as, for example, to return to the basic function of live image display.

In this connection, the present invention is not limited to live image display, but may also be used for still image display, in which mode the motion of the object-moving device is changed by moving the sample image relative to the display area, as has been partly described earlier herein. As explained, the magnification can then be adjusted by digital means (digital zoom).

All in all, the direct conversion of the motion of input means and the adjustment of the field of view allow very intuitive control of a microscope of the type under discussion. This applies similarly to more complex functions, such as measurement, image processing, annotation, and the like. Accordingly, the present invention can replace a number of conventional input devices, such as hand controls, joysticks, a computer mouse, keyboards, and the like, and thus significantly reduce the complexity of such a microscope system, and in particular also the space requirements and cost thereof.

Figure 1:
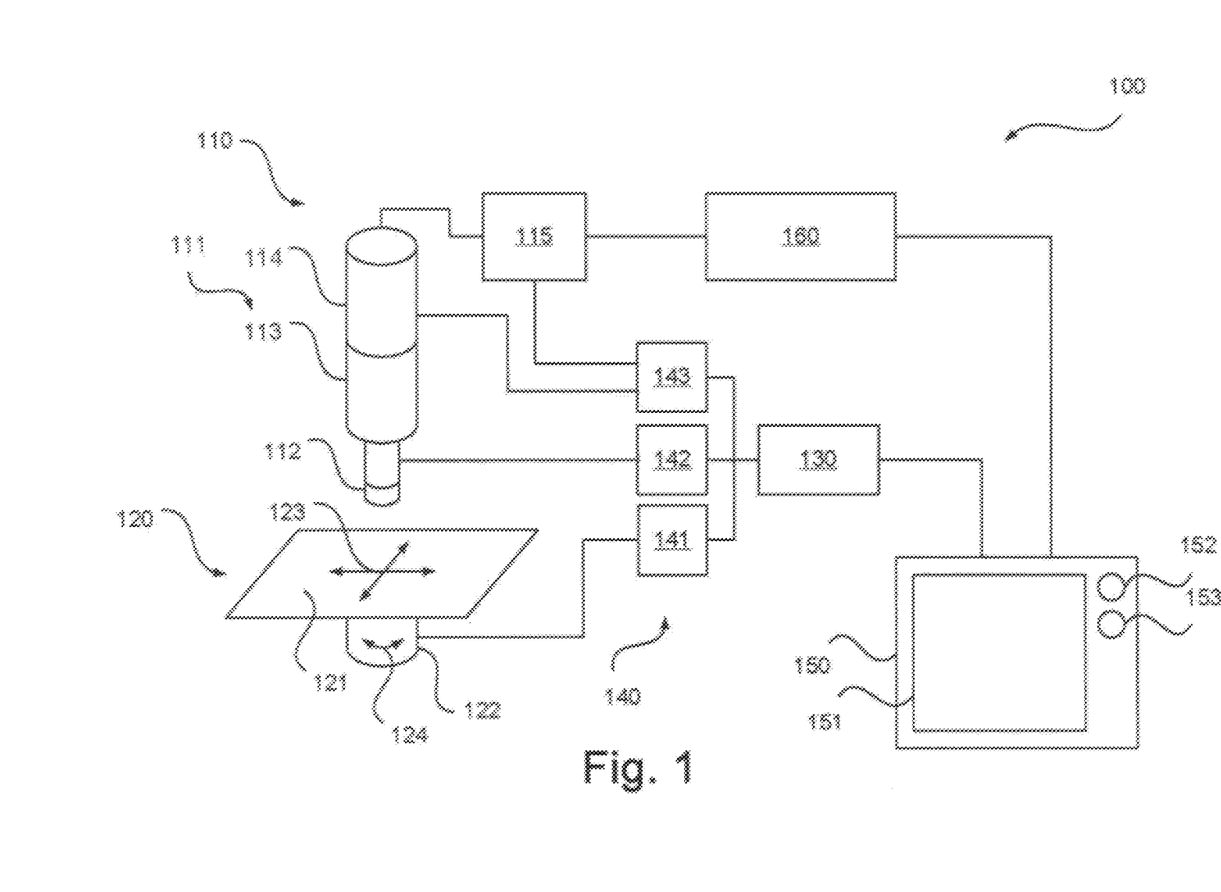
FIG. 1 is a schematic view of a microscope according to an embodiment of the present invention.

Referring to FIG. 1, a microscope according to an embodiment of the present invention is shown schematically and generally designated 100.

Microscope 100 has an image acquisition system 110 including optical components 111, for example, an objective 112 and a tube 113, and preferably having a suitable optical zoom system. Also provided are electronic components, for example, a sensor 114 in the form of a CCD chip and a digital image processing system 115. Image processing system 115 may be completely or partially integrated into image acquisition system 110, or arranged in a downstream control/processing means 160, such as a computer, or a separate, independent unit 115.

An optical image captured by optical components 111 is converted into a digital image and advantageously already suitably processed by means of sensor 114 and digital image processing system 115.

An object-moving device 120 is provided, for example in the form of a manual or motorized xy cross stage 121 or rotary stage having a suitable translation and rotation device 122 which allows object-moving device 120 to be translated and/or rotated in the directions of arrows 123 and 124. Analogously, the rotation may also be achieved by rotating the optical axis of image acquisition system 110 or sensor 114.

Microscope 100 further has a control device 130 for controlling adjusting elements 141, 142 and 143, which are associated with individual components of microscope 100 and form part of an adjusting unit 140. This makes it possible, for example, to adjust object-moving device 120 or to change the settings of optical elements 111 and electronic elements 114, 115 of image acquisition system 110. Control device 130 operates based on inputs sensed by touch screen 150.

Touch screen 150 has a display area 151, in which is displayed a live image or a still image of the object captured by image acquisition system 110, and in which the inputs mentioned above can be made especially using one or more fingers of a user as input means. Additional input means 152, 153, such as switches or keys, may also be provided. Similarly, additional control and/or processing means 160 may be provided, for example, in the form of a computer 160.

Figure 2:
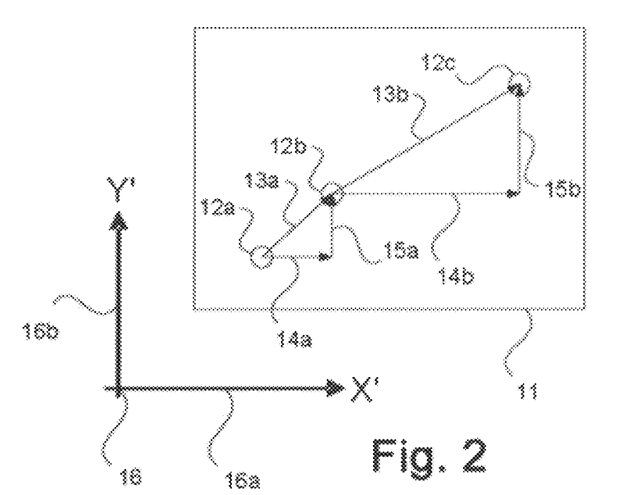
FIG. 2 is a schematic view illustrating a translation motion according to an embodiment of the present invention.

Referring to FIG. 2, there is illustrated, in schematic form, a movement of a contact point of an input means on a display area of a touch screen, such as display area 151 of touch screen 150 of the microscope 100 shown in FIG. 1.

A live or still image produced by a suitable image acquisition system, such as the above-described image acquisition system 110, is displayed in a display area 11 (which corresponds to the above-described display area 151). The entire display area 11 has a touch-sensitive surface. In area 11, positions of contact points of input means and/or changes in position of such contact points over time can be detected simultaneously. To this end, the positions of such contact points are scanned at a predetermined scanning rate while in contact. Contactless sensing is also possible. Ultimately, data on the positions 12a, 12b, 12c of the respective contact point are thereby acquired sequentially over time. The distance between two positions, for example, between positions 12a and 12b or between positions 12b and 12c, represents the movement over time. The corresponding control information includes distance, speed, and acceleration in a coordinate system with axes X', 16a and Y', 16b, and a point of origin 16. The axes of the coordinate system are parallel to the edges of display area 11.

Figure 3:
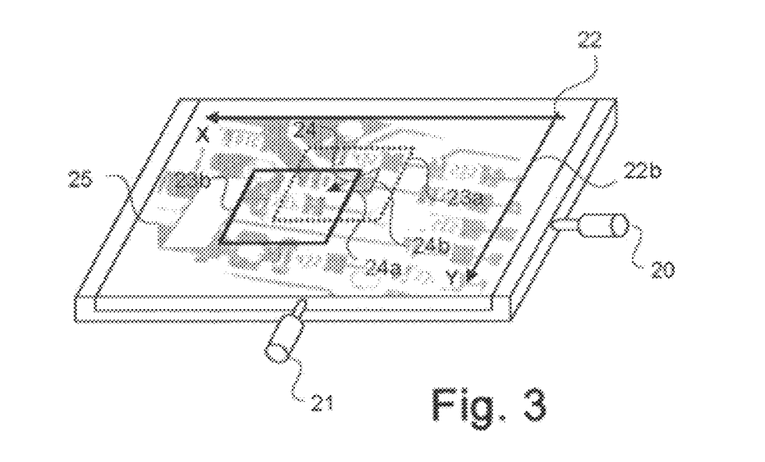
FIG. 3 is a schematic view of a translation device according to an embodiment of the present invention.

Turning now to FIG. 3, there is illustrated, in schematic form, the motion of an object-moving device, such as object-moving device 120 of microscope 100.

The object-moving device has orthogonal motorized actuators 20, 21 adapted to move the object-moving device along axes of motion X and Y. Actuators 20, 21 are used to move an object 25 located on the object-moving device relative to the field of view, so that the field of view moves from a position 23a to a position 23b on the object as actuators 20, 21 move. In a system with image inversion, the orientation of X and Y is opposite to that of the axes X' and Y' described in connection with FIG. 2.

The total magnification $M_{tot}$ of the imaging system is defined as the ratio of the size of the display area to the size of the field of view that is visible in the display area. The scaling of axes X, Y and X', Y' is proportional to $M_{tot}$. When a contact point is detected in image display area 151 (FIG. 1) or 11

(FIG. 2), respectively, the motion data thereof (distance, speed, acceleration) are used to control actuators 20, 21 of the object-moving device taking $M_{tot}$ into account.

In the situation depicted in FIG. 3, no rotation command is detected. Therefore, motion component 14a of contact point 12a along X' is directly converted into a motion 24a along axis X. This applies analogously to motion component 15a along Y', which results in a motion 24b along axis Y. This motion is performed taking into account the speed and acceleration of the respective contact point.

Figure 4A:
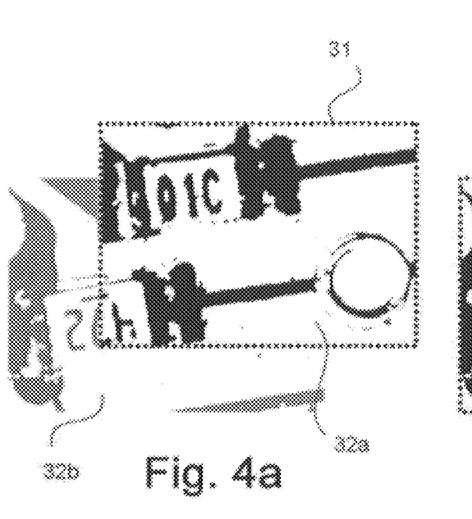
FIG. 4 is a schematic view illustrating a translation of an image region according to an embodiment of the present invention.
Figure 4B:
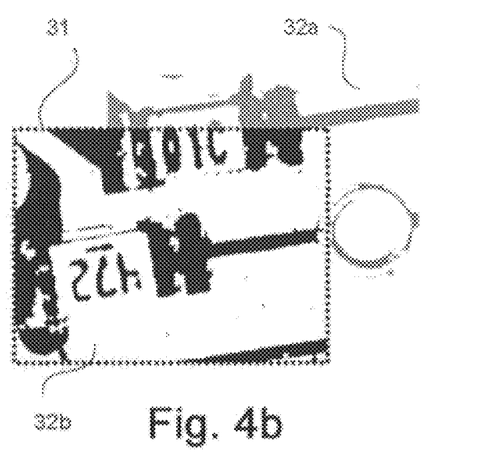

Referring to FIG. 4, there is illustrated a motion of an image in the image area. The motion of object-moving device 120, as described earlier in connection with FIGS. 1 through 3, causes the field of view displayed in a display area 31 to be moved from a position 32a to a position 32b. FIG. 4a depicts the situation before the movement; FIG. 4b depicts the situation after the movement. The distance between two corresponding points before and after the movement of the object-moving device corresponds to the motion data of a contact point detected in a display area 151 or 11, respectively. However, another alternative for moving display area 31 can also be illustrated with reference to FIG. 4. If the image captured by sensor 114 (cf. FIG. 1) is larger than the display area 31 offered to the user, a translation or shift command can also be implemented in a purely digital manner without moving object-moving device 20 (cf. FIG. 1), as long as the desired shift of display area 31 is still within the image captured by sensor 114 (cf. FIG. 1). For this purpose, display area 31 is shifted from position 32a to position 32b merely by correspondingly moving the image portion that is read out for display on touch screen 150 (cf. FIG. 1).

Figure 5:
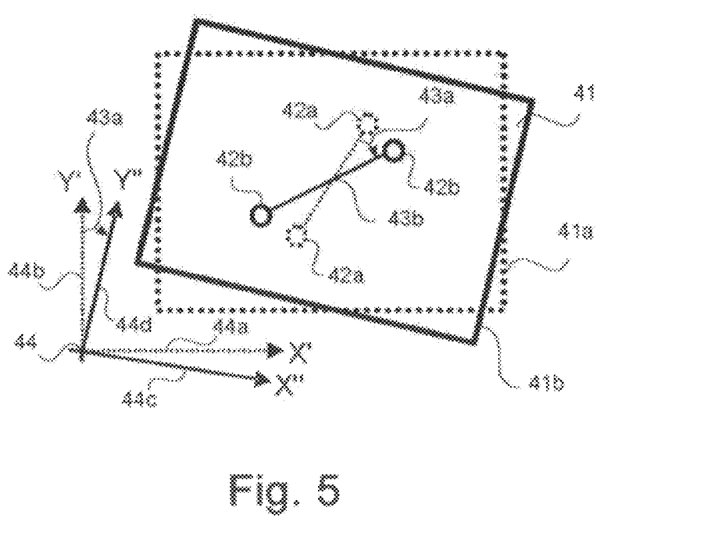
FIG. 5 is a schematic view illustrating an image rotation according to an embodiment of the present invention.

Referring to FIG. 5, there is illustrated the conversion of a rotation command recognized from the motion of two contact points of input means on a display area of a touch screen. The motion data is used to rotate the field of view from a position 41a to a position 41b and to simultaneously rotate the associated coordinate system with the axes X" and Y", 44a-d, about a point of origin 44 with respect to display area 41. The center of rotation is defined by intersection point 43b. The intersection point is defined by the connecting line 42a between the two contact points before the movement and the connecting line 42b between the two contact points after the movement. The angle of rotation is defined by the angle of intersection 43a at intersection point 43b.

Turning now to FIG. 6, there are illustrated, in schematic form, a rotation and a zoom of an image in a display area. FIG. 6a shows the field of view 51 prior to a rotation in display area 50. The display area shows the image with a scale 54, which results from the total magnification $M_{tot}$ of the imaging system.

Figure 6A:
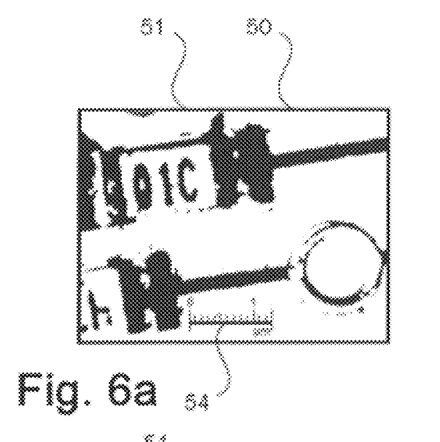
FIG. 6 is a schematic view illustrating an image rotation according to an embodiment of the present invention.
Figure 6B:
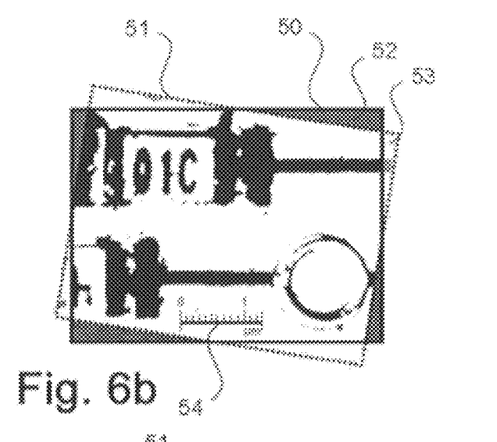

FIG. 6b shows the field of view after a motion of the aforedescribed type. The rotation does not change scale 54 of the image. The purpose of this rotation is to better align regions of interest with the coordinate system of the display area to allow for better documentation. However, it can also be clearly seen in FIG. 6b that certain regions 52 of the original field of view are no longer visible in display area 53. On the other hand, new regions 52 created in the image area as a result of this rotation do not contain any image information because they are outside of the image portion that is read out. This occurs only if the field of view is rotated by performing image processing on the digital image. If the field of view is rotated by rotating the object-moving device 120, such regions without image information will not be created.

Figure 6C:
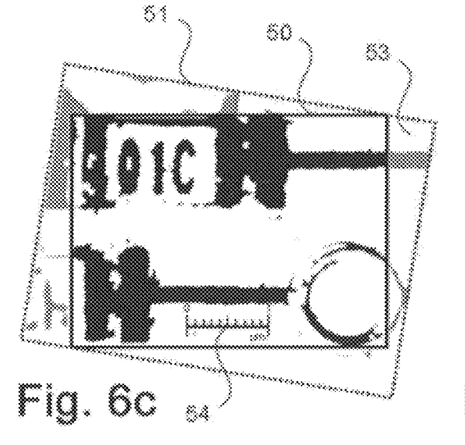
Figure 6D:
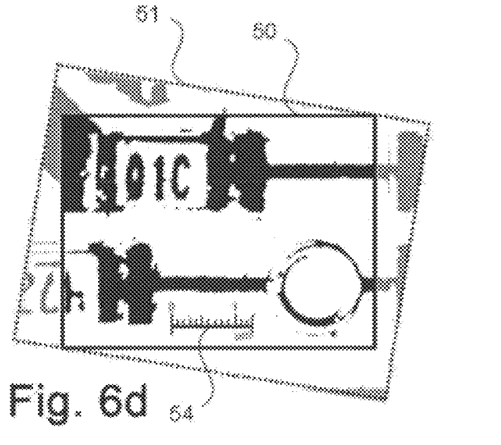

Therefore, in FIG. 6c, field of view 51 is scaled using digital processing means, so that the image 53 of the field of view covers all parts of display area 50. This results in a magnification factor $M_{DIG}$ for this scaling process. Ultimately, scale 54 of the image in display area 50 has changed by the factor $M_{DIG}$. However, this is not desired and can therefore be compensated for by changing the magnification of the optical zoom by a factor of $1/M_{DIG}$, as is illustrated in FIG. 6d. Field of view 51 in display area 50 corresponds to the one before the rotation again (cf. FIG. 6a).

The steps, which are shown sequentially in FIGS. 6a through 6d, are preferably performed in parallel. The rotation of the field of view can be performed either using digital processing means or by rotating the optical axis of the imaging system. After rotation of the field of view, all lateral movements of the field of view (see FIG. 2) are converted from the coordinate system of the display area to the coordinate system of the object-moving device using the angle of rotation 43a (cf. FIG. 5).

Figure 7A:
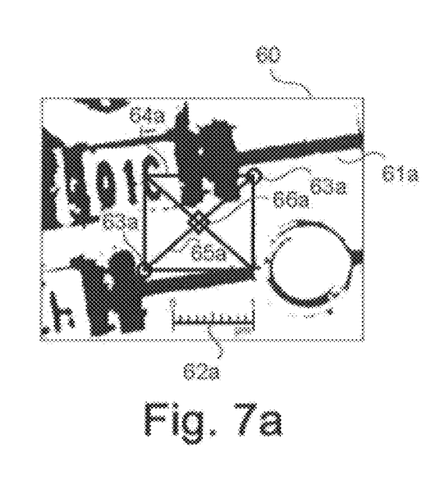
FIG. 7 is a schematic view illustrating a zoom operation according to an embodiment of the present invention.

Referring to FIG. 7, there is shown a magnification of the field of view. The image of a first field of view 61a is shown in FIG. 7a in a display area 60 prior to magnification. The scale of the image is illustrated by size scale 62a. The position of two contact points 63a defines a rectangular region 64a, whose edges are parallel to display area 60.

Figure 7B:
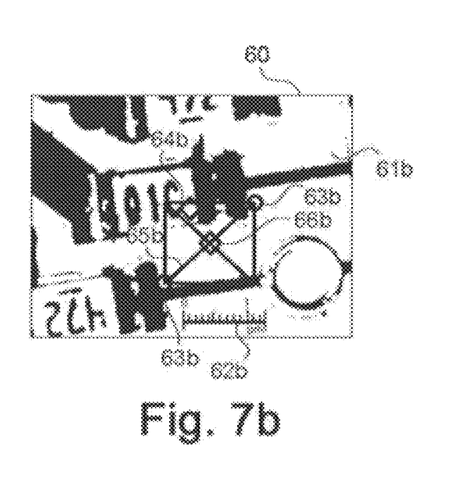

FIG. 7b depicts the situation after the size of the visual field has been changed. The position of the two contact points, now referred to as 63b, has changed with respect to their position 63a in FIG. 7a, and the size of second rectangular region 64b has decreased accordingly. The change of the field of view has been brought about by changing $M_{tot}$. Similarly, the ratio of $M_{tot}$ of fields of view 61a, 61b is defined by the ratio of the two diagonals 65a, 65b of the two rectangular regions 64a, 64b. The change in $M_{tot}$ also changes the scale of the image, as is illustrated by the size scale 62b depicted in FIG. 7b. The ratio of the two scales corresponds to the ratio of the values of $M_{tot}$.

The change in $M_{tot}$ can be brought about using digital zoom means. This is advantageous in particular when the method is used to change the size of still images. On the other hand, for purposes of live image display, it will be advantageous for $M_{tot}$ to be changed using optical means, such as an optical zoom.

In all cases, it is preferred to observe a specific aspect ratio criterion when changing the image size. A preferred aspect ratio criterion is, for example, a 1:1 ratio of camera pixels to image pixels. When the optical zoom reaches its upper magnification limit, $M_{tot}$ can be further increased using a digital zoom. For purposes of reducing $M_{tot}$, it is preferred to first reduce the digital zoom until the aspect ratio criterion is met. Further reduction is then accomplished using the optical zoom.

Other aspect ratio criteria may provide, for example, that the optical resolution of the imaging system must be equal to the size of a pixel of the display area. It is also possible to include additional criteria as desired. The two rectangular regions 64a, 64b shown in FIG. 7 have a center point 66a and 66b, respectively. These center points, which are also used for centering purposes, may be changed during magnification or size changes. The motion of the center point is converted into the motion of the object-moving device, as has been explained in connection with FIG. 3.

Figure 8A:
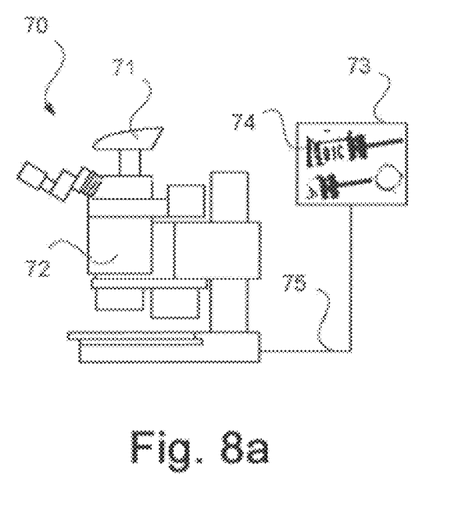
FIG. 8 is a schematic view showing microscopes according to preferred embodiments of the present invention.
Figure 8B:
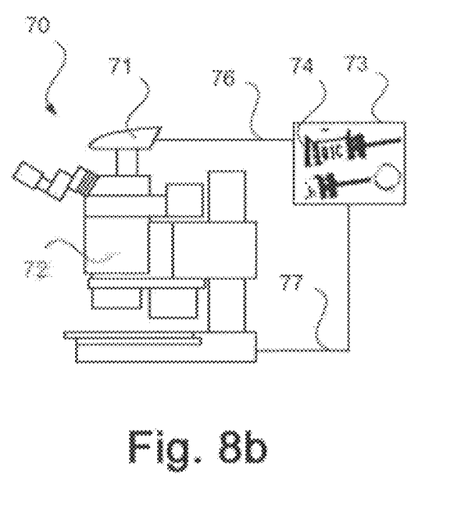

Referring now to FIGS. 8a and 8b, there are shown further microscopes 70 of preferred embodiments. For the sake of clarity, not all of the elements depicted in FIG. 1 are specifically shown here. In particular, microscope unit 72 may include components 112 and 113 from FIG. 1, camera 71 may include components 114, 115 and 160, and image display 73 may include component 150 from FIG. 1.

A microscope, as shown in FIG. 8a, includes a microscope unit 72, a camera 71, and an image display 73 as the main components. Image display 73 has a touch screen; i.e. a touch-sensitive image display area 74, as described hereinbefore. In FIG. 8*a*, a single connection 75 between microscope unit 72, camera 71 and image display unit 73 is used for communication. Moreover, this connection 75 can also be used for supplying electric power to microscope unit 72 and camera 71.

FIG. 8*b* shows another embodiment, where two connection lines are provided, including a connection line 76 adapted for connection to camera 71, and a connection line 77 adapted for connection to microscope unit 72. Each of these connection lines may provide a communication link and/or electric power. The communication may be performed based on known, collectively or separately used communications standards, such as USB, Firewire, CAN, HDMI, etc. or wirelessly via WLAN, Bluetooth, infrared etc.

While the invention has been particularly shown and described with reference to preferred embodiments thereof, it will be understood by those skilled in the art that various changes in form and details may be made therein without departing from the spirit and scope of the invention.

LIST OF REFERENCE NUMERALS

11 display area
12*a*, 12*b*, 12*c* position
14*a*, 14*b* motion component
15*a*, 15*b* motion component
16 point of origin
16*a* X' axis
16*b* Y' axis
20, 21 actuator
23*a*, 23*b* position
24*a*, 24*b* motion component
25 object
31 display area
31*a*, 32*b* position
41 display area
41*a*, 41*b* position
42*a*, 42*b* contact point
43*a* angle of intersection
43*b* intersection point
44 point of origin
44*a* X' axis
44*b* Y' axis
44*c* X" axis
44*d* Y" axis
50 display area
51 field of view
52 image region
53 field of view
54 scale
60 display area
61*a*, 61*b* field of view
62*a*, 62*b* size scale
63*a* contact point
64*a*, 64*b* region
65*a*, 65*b* diagonal
66*a*, 66*b* center point
70 microscope
71 camera
72 microscope unit
73 image display
74 touch screen
75 connection
76, 77 connection line
100 microscope
110 image acquisition system
111 optical components
112 objective
113 tube
114 sensor
115 image processing system
120 object-moving device
121 cross-stage
122 translation and rotation device
123 arrow for translation
124 arrow for rotation
130 control device
140 adjusting unit
141, 142, 143 adjusting element
150 touch screen
151 display area
152, 153 input means
160 control/processing means

What is claimed is:

1. A microscope comprising:
an image acquisition system configured to optically and digitally image an object so as to produce an object image;
microscope components including at least one of an objective turret including at least one objective, a zoom adjust and a focus drive movable in a z-direction that are at least one of motorized and electrically controllable; and
a touch screen configured to display the object image in a display area thereof and to sense motions of an input object in the display area within the displayed object image so as to cause the microscope components to move in a corresponding manner,
wherein sensing a first one of the motions of the input object corresponding to a rotation command within the displayed object image causes a change in an alignment of the object image in a coordinate system of the display area.

2. The microscope as recited in claim 1, wherein the display area of the touch screen, within the displayed object image, is configured to detect acceleration of the input object on or near a surface of the touch screen.

3. The microscope as recited in claim 2, wherein the microscope is configured to derive control signals from the sensed motion or detected acceleration, the control signals being adapted to control functions of the microscope components.

4. The microscope as recited in claim 1, wherein the microscope components include optical and digital components of the image acquisition system.

5. The microscope as recited in claim 4, wherein the optical and digital components of the image acquisition system include at least one of an image acquisition system, an imaging sensor, a digital camera, an image processing system, a control, a processor, an x-y adjustable microscope stage, a cross stage and a rotary stage.

6. The microscope as recited in claim 1, wherein the display area of the touch screen, within the displayed object image, is configured to sense at least one of a relative position, a relative motion and a relative acceleration of a plurality of input objects with respect to one another on or near a surface of the touch screen so as to cause the corresponding motions of the microscope components.

7. The microscope as recited in claim 1, wherein the display area of the touch screen, within the displayed object image, includes a multi-touch screen.

8. The microscope as recited in claim 1, wherein the display area of the touch screen, within the displayed object image, includes at least one of an acoustic pulse sensor, a surface-wave sensor, a capacitive sensor, a bending wave sensor, a resistive sensor, an optical sensor and an infrared sensor configured to sense the inputs.

9. The microscope as recited in claim 1, further comprising at least one of an object-moving device, an optical unit and a digital image processing system, wherein a change in the settings of the microscope affects the at least one of the object-moving device, optical unit and digital image processing system.

10. The microscope as recited in claim 1, wherein the image acquisition system is configured to produce a live image as the object image.

11. The microscope as recited in claim 1, wherein the microscope is configured, based on receiving a second one of the motions of the input object corresponding to a translation command after the rotation command, to convert lateral movements of the field of view from the coordinate system of the display area to a coordinate system of the microscope using an angle of rotation of the first one of the motions of the input object.

12. A control device for controlling a microscope that includes:
an image acquisition system configured to optically and digitally image an object so as to produce an object image;
microscope components including at least one of an objective turret including at least one objective, a zoom adjust and a focus drive movable in a z-direction that are at least one of motorized and electrically controllable; and
a touch screen configured to display the object image in a display area thereof and to sense motions of an input object in the display area within the displayed object image for changing settings of the microscope components,
the control device including an input configured to receive the motions of the input object sensed at least in the display area of the touch screen within the displayed object image and at least one output configured to cause the microscope components to move in a corresponding manner,
wherein sensing a first one of the motions of the input object corresponding to a rotation command within the displayed object image causes a change in an alignment of the object image in a coordinate system of the display area.

13. The control device as recited in claim 12, wherein the control device is configured, based on receiving a second one of the motions of the input object corresponding to a translation command after the rotation command, to convert lateral movements of the field of view from the coordinate system of the display area to a coordinate system of the microscope using an angle of rotation of the first one of the motions of the input object.

14. A method for operating a microscope including an image acquisition system configured to optically and digitally image an object so as to produce an object image; and
microscope components including at least one of an objective turret including at least one objective, a zoom adjust and a focus drive movable in a z-direction that are at least one of motorized and electrically controllable; the method comprising:
providing the microscope with a touch screen configured to display the object image in a display area and to sense motions of an input object in the display area for changing settings of the microscope components; and
sensing the motions of the input object in the display area of the touch screen within the displayed object image and moving the microscope components based on the sensed motions,
wherein sensing a first one of the motions of the input object corresponding to a rotation command within the displayed object image causes a change in an alignment of the object image in a coordinate system of the display area.

15. The method recited in claim 14, further comprising recognizing commands in the display area of the touch screen, the commands including at least one of translation commands, zoom commands, center commands, focus commands, selection commands, measurement commands, processing commands, interrogation commands and function commands.

16. The method recited in claim 15, wherein the recognizing commands includes recognizing a defined number of input objects being at least one of brought into contact with a surface of the display device, maintaining contact with or near the surface for a defined period of time, being brought into contact with the surface a defined number of times, and being brought into contact with or near the surface at a defined number of positions.

17. The method as recited in claim 15, wherein the recognizing commands includes recognizing a translation command when at least one input object is positioned in contact with a surface of the display area of the touch screen and moved from a contact position relative to the surface.

18. The method as recited in claim 15, wherein the recognizing commands includes recognizing the rotation command when a plurality of input objects are positioned in contact with a surface of the display area of the touch screen at an initial position and the plurality of input objects are jointly rotated from the initial position relative to the surface.

19. The method as recited in claim 15, wherein the recognizing commands includes recognizing a zoom command when a plurality of input objects are positioned in contact with a surface of the display area of the touch screen and a relative distance between the input objects is changed from a starting position relative to the surface.

20. The method as recited in claim 15, wherein the object image produced by at least one of optical components and digital components of the image acquisition system is at least one of translated, centered and focused when at least one of a respective translation command, a zoom command, a center command and a focus command is recognized in the display area of the touch screen.

21. The method as recited in claim 20, wherein the object image is a live image and wherein the at least one translating, centering and focusing the object image is carried out at least by a change in a setting of at least one of optical and digital components of the image acquisition system.

22. The method as recited in claim 21, wherein the at least one of optical and digital components includes at least one of a magnification changer, a tube, an object moving device, a microscope stage with a translation device, a microscope stage with a rotation device and an illumination device of the microscope.

23. The method as recited in claim 15, wherein a region of an object image produced by the image acquisition system is at least one of selected, measured, processed and integrated when at least one of as respective selection command, a measurement command, a processing command, and an integration command is recognized in the display area of the touch screen.

24. The method as recited in claim 15, further comprising performing a function change to a different mode of operation of the microscope when a function change command is recognized.

25. The method as recited in claim 24, wherein the performing the function change results in a change in an input mode for recognizing commands based on inputs sensed on the touch screen.

26. The method as recited in claim 25, wherein the microscope includes a plurality of input modes and each input mode is associated with a number of recognizable commands.

27. The method as recited in claim 14, further comprising, based on receiving a second one of the motions of the input object corresponding to a translation command after the rotation command, converting lateral movements of the field of view from the coordinate system of the display area to a coordinate system of the microscope using an angle of rotation of the first one of the motions of the input object.

* * * * *